US010532018B2

(12) United States Patent
Kang et al.

(10) Patent No.: US 10,532,018 B2
(45) Date of Patent: Jan. 14, 2020

(54) METHOD OF WHITENING SKIN USING TRANEXAMIC ACID-PEPTIDE HAVING SKIN WHITENING ACTIVITY

(71) Applicant: ANPEP INC., Cheongju-si, Chungcheongbuk-do (KR)

(72) Inventors: Sang Moon Kang, Daejeon (KR); Seock Yeon Hwang, Daejeon (KR); Mi Hye Lim, Yongin-si (KR); Chung Park, Daejeon (KR); Eun Jin Shin, Cheongju-si (KR); Kee-young Lee, Cheongju-si (KR); Un Kyu Park, Daejeon (KR); Hyun Ji Lim, Daejeon (KR); Dong Hyun Yang, Daegu (KR); Sang Joo Cha, Goyang-si (KR)

(73) Assignee: ANPEP INC., Cheongju-si, Chungcheongbuk-Do (KR)

( * ) Notice: Subject to any disclaimer, the term of this patent is extended or adjusted under 35 U.S.C. 154(b) by 0 days.

(21) Appl. No.: 16/305,492

(22) PCT Filed: Jun. 29, 2017

(86) PCT No.: PCT/KR2017/006919
§ 371 (c)(1),
(2) Date: Nov. 29, 2018

(87) PCT Pub. No.: WO2018/004281
PCT Pub. Date: Jan. 4, 2018

(65) Prior Publication Data
US 2019/0380943 A1 Dec. 19, 2019

(30) Foreign Application Priority Data
Jun. 29, 2016 (KR) .......................... 10-2016-0081998

(51) Int. Cl.
*A61K 8/64* (2006.01)
*A61Q 19/02* (2006.01)
*A61K 38/05* (2006.01)
*A61K 8/41* (2006.01)

(52) U.S. Cl.
CPC .................. *A61K 8/64* (2013.01); *A61K 8/41* (2013.01); *A61K 38/05* (2013.01); *A61Q 19/02* (2013.01)

(58) Field of Classification Search
None
See application file for complete search history.

(56) References Cited

FOREIGN PATENT DOCUMENTS

| JP | H05-170637 A | | 7/1993 | |
|---|---|---|---|---|
| JP | H06-072846 A | | 3/1994 | |
| JP | H06072846 A | * | 3/1994 | ............... A61K 7/48 |
| JP | H06-345797 A | | 12/1994 | |
| JP | 07165556 A | * | 6/1995 | ............... A61K 7/48 |
| KR | 10-2004-0060157 A | | 7/2004 | |
| KR | 1020100092150 | * | 12/2009 | ............... A61K 8/64 |
| KR | 10-2010-0092150 A | | 8/2010 | |

OTHER PUBLICATIONS

International Search Report for PCT/KR2017/006919 dated Dec. 12, 2017 from Korean Intellectual Property Office.

* cited by examiner

*Primary Examiner* — Lianko G Garyu
(74) *Attorney, Agent, or Firm* — Paratus Law Group, PLLC

(57) ABSTRACT

A skin whitening method including: administering to a subject a cosmetic composition including a tranexamic acid-peptide having skin whitening activity selected from the group consisting of Tranexamil-AS, Tranexamil-AT, Tranexamil-AP, Tranexamil-GP, Tranexamil-ES, Tranexamil-KK, Tranexamil-HK, Tranexamil-MY, Tranexamil-GH, Tranexamil-MA, Tranexamil-AH, Tranexamil-CC, Tranexamil-SA, Tranexamil-WA, Tranexamil-WE, Tranexamil-KD, Tranexamil-NA, Tranexamil-TS, Tranexamil-SS, Tranexamil-EC, Tranexamil-TA, Tranexamil-PF, Tranexamil-VS, Tranexamil-VV, Tranexamil-VP, Tranexamil-AA, Tranexamil-PS, Tranexamil-HA, Tranexamil-GK, Tranexamil-KV, Tranexamil-AR, Tranexamil-RP, Tranexamil-PQ, Tranexamil-QG, Tranexamil-PP, Tranexamil-VR, Tranexamil-SV, Tranexamil-ET, Tranexamil-CG and Tranexamil-NT.

6 Claims, 10 Drawing Sheets
Specification includes a Sequence Listing.

METHOD OF WHITENING SKIN USING TRANEXAMIC ACID-PEPTIDE HAVING SKIN WHITENING ACTIVITY

CROSS REFERENCE TO PRIOR APPLICATIONS

This application is a National Stage Patent Application of PCT International Patent Application No. PCT/KR2017/006919 filed Jun. 29, 2017 under 35 U.S.C. § 371, which claims priority to Korean Patent Application No. 10-2016-0081998 filed Jun. 29, 2016, which are all hereby incorporated by reference in their entirety.

BACKGROUND

The present invention relates to a tranexamic acid-peptide having skin whitening activity and a use thereof, and more specifically, to a tranexamic acid-peptide of a particular sequence with an excellent skin whitening effect, thermal stability, and storage stability, and a use thereof.

Skin is the largest tissue in the body and functions to protect the body from sunlight, physical and chemical stimuli, and it is absolutely necessary for the maintenance of human life and is constantly regenerated to maintain homeostasis. The skin is composed of the epidermis, the dermis, and the subcutaneous fat in order from the outer side. The epidermis, which is the thinnest tissue of the skin, plays an important role of moisturizing and protecting the skin, and is responsible for preventing water loss, damage, bacterial invasion, etc. Skin is a tissue that surrounds the entire body and has various functions. Because it has a barrier function between the inside and the outside of the body, it has an immune system by the islets of Langerhans and a moisture control function by the epidermis. Additionally, it performs the synthesis of vitamin D under a proper sunlight and also the excretion into the lipid reservoir and sweat glands. The stratum corneum produced by the normal differentiation process in healthy skin has the function of maintaining the moisturization of the skin and protecting it from the stimulation of the external environment. This function is called the skin barrier function and it may be the most important role of the epidermis.

Activity of many enzymes involved in melanin synthesis and skin tone with regard to skin whitening, one of the major effects of cosmetics, have been elucidated. However, the reasons why the skin color of Asian people is particularly susceptible to deposits and aging have not yet been identified. Materials that are believed to reveal skin tone are typically known to inhibit melanin synthesis and each of the enzymes involved therein.

A person's skin color varies depending on various factors, in particular season, race, and sex, and it is mainly determined by the amount of melanin, carotene, and hemoglobin, and among these, melanin is the most crucial factor. Melanin is synthesized in melanocytes present in the basal layer of the skin and transferred into adjacent keratinocytes thereby exhibiting the human skin colors. It is known that when the melanin level is abnormally low, skin lesions such as vitiligo are induced, whereas when melanin is produced excessively, spots and blemishes are formed. Melanin is produced by the action of tyrosinase on tyrosine (i.e., a kind of amino acid), tyrosinase is more activated by ultraviolet rays. Therefore, when the skin is exposed excessively to sunlight, it turns black. Cosmetics in the concept of the skin whitening effect are establishing a big market in Korea, Japan, etc. and these products are prepared by combining materials that usually have the inhibitory effect against tyrosinase.

Recently, the activity of many enzymes related to melanin synthesis and skin tone has been elucidated, however, the reasons why the skin color of Asian people is particularly susceptible to deposits and aging have not yet been identified. Materials that are believed to reveal skin tone are typically known to inhibit melanin synthesis and each of the enzymes involved therein.

Conventionally, examples of the raw materials that can be incorporated into skin whitening cosmetics as an inhibitor of tyrosinase activity not only include plant extracts (e.g., ascorbic acid (vitamin C) and derivatives thereof, a *Morus alba* L. extract, a green tea extract, an aloe extract, a Scutellaria radix extract, etc.), but also include kojic acid, Arbutin, an oil-soluble licorice extract, tranexamic acid, amide, etc. However, various plant extracts have a problem in that they are unstable, and the effects cannot be sustained when mixed into a product and that their effects of inhibiting tyrosinase activity are not significant. Additionally, kojic acid is commonly used as a tyrosinase inhibitor but it has problems in that it is difficult to prepare it as a composition because it may cause allergic reactions (Nakagawa M. et. al., Contact Dermatitis, 43: PP9-3(1995)), and that it should be used in an excessive amount close to 2% because it is unstable in products.

Tranexamic acid is an analog of lysine, which is a kind of amino acid. It has been widely used as a hemostatic agent in pharmaceutical field and it is a material which has been proved with regard to its administration frequency and safety so as to be one of the essential drugs prescribed by the World Health Organization. Tranexamic acid has the role of aiding the hemostatic activity by inhibiting the activation of the active site of plasmin, an anticoagulant in the blood. However, plasmin not only promotes blood clotting but also promotes the growth of melanocytes, which are the cells that produce melanin, and simultaneously, activates the production of arachidonic acid, which is the precursor of prostaglandins and leucotrienes that promote the production of melanin. Therefore, plasmin has a significant effect on the intracellular melanin production and helps skin whitening by inhibiting the activity of plasmin.

Meanwhile, various attempts have been made to develop various whitening agents using peptides, but their effects were not significant. Additionally, there was a difficulty in the manufacture of vitamin C-peptide complexes and hydroquinone peptide complexes for the purpose of maximizing the whitening effects, and its use was limited due to the high cost, and thus its application in the market was not remarkable.

The majority of whitening functional materials currently on the market are focused on alleviating the symptomatic parts by eliminating the sites for melanin pigment accumulation, and conventional dermatologic procedures also aim at artificially removing these accumulation sites through a laser.

Removing only these symptomatic parts may have a short-term effect, however, it does not accompany an improvement in the turnover, which is the principal cause, and thus a side effect occurs that melanin accumulates again in a short period of time. Accordingly, if it is possible to restore the skin's normal turnover cycle, and prevent and eliminate hyperkeratosis of the skin through moisturizing action, it is expected that the principal cause of the pigment accumulation can be resolved instead of an attempt being focused on resolving symptomatic matters, and a change into a healthy skin may be achieved.

SUMMARY

Accordingly, the present invention has been made to solve the above problems, and the present invention aims at developing a new highly-functional whitening material, in which the disadvantages of existing whitening materials are overcome, by carrying out the clinical efficacy of tranexamic acid-peptide and development of cosmetic formulations, and providing a tranexamic acid-peptide, which has skin whitening activity that is able to induce a whitening effect through an improvement in skin turnover and restoration of a healthy skin, and a use thereof.

To solve the above problems, a first aspect of the present invention provides a tranexamic acid-peptide, having skin whitening activity, selected from the group consisting of Tranexamil-AS, Tranexamil-AT, Tranexamil-AP, Tranexamil-GP, Tranexamil-ES, Tranexamil-KK, Tranexamil-HK, Tranexamil-MY, Tranexamil-GH, Tranexamil-MA, Tranexamil-AH, Tranexamil-CC, Tranexamil-SA, Tranexamil-WA, Tranexamil-WE, Tranexamil-KD, Tranexamil-NA, Tranexamil-TS, Tranexamil-SS, Tranexamil-EC, Tranexamil-TA, Tranexamil-PF, Tranexamil-VS, Tranexamil-VV, Tranexamil-VP, Tranexamil-AA, Tranexamil-PS, Tranexamil-HA, Tranexamil-GK, Tranexamil-KV, Tranexamil-AR, Tranexamil-RP, Tranexamil-PQ, Tranexamil-QG, Tranexamil-PP, Tranexamil-VR, Tranexamil-SV, Tranexamil-ET, Tranexamil-CG, and Tranexamil-NT.

Additionally, the present invention provides a tranexamic acid-peptide which is characterized by inhibiting melanin synthesis.

Additionally, the present invention provides a tranexamic acid-peptide which is characterized by inhibiting the activity of tyrosinase.

Additionally, the present invention provides a tranexamic acid-peptide which is characterized by inhibiting the expression of microphthalmia-associated transcription factor (MITF).

Additionally, the present invention provides tranexamic acid-peptides which are characterized by having a skin whitening effect at a concentration of 0.01% to 5.0%.

Additionally, the present invention provides tranexamic acid-peptides which are characterized by having increased stability by tranexamic acid at its N-terminus.

A second aspect of the present invention provides a composition for skin whitening, containing a tranexamic acid-peptide selected from the group consisting of Tranexamil-AS, Tranexamil-AT, Tranexamil-AP, Tranexamil-GP, Tranexamil-ES, Tranexamil-KK, Tranexamil-HK, Tranexamil-MY, Tranexamil-GH, Tranexamil-MA, Tranexamil-AH, Tranexamil-CC, Tranexamil-SA, Tranexamil-WA, Tranexamil-WE, Tranexamil-KD, Tranexamil-NA, Tranexamil-TS, Tranexamil-SS, Tranexamil-EC, Tranexamil-TA, Tranexamil-PF, Tranexamil-VS, Tranexamil-VV, Tranexamil-VP, Tranexamil-AA, Tranexamil-PS, Tranexamil-HA, Tranexamil-GK, Tranexamil-KV, Tranexamil-AR, Tranexamil-RP, Tranexamil-PQ, Tranexamil-QG, Tranexamil-PP, Tranexamil-VR, Tranexamil-SV, Tranexamil-ET, Tranexamil-CG, and Tranexamil-NT.

Additionally, the composition provides a composition for skin whitening characterized in that the composition is a cosmetic composition.

According to the present invention, tranexamic acid-peptides have an excellent effect on skin whitening by inhibiting melanin production, and has excellent stability and skin permeability, and thus they are effective for the production of a cosmetic composition for skin whitening more effective compared to the existing cosmetic compositions.

DETAILED DESCRIPTION

Hereinafter, the present invention will be described in more detail with reference to examples.

These embodiments are only intended to further illustrate the present invention, and it will be apparent to those skilled in the art that the scope of the present invention is not limited by these embodiments in accordance with the gist of the present invention.

The present inventors have examined the skin whitening effect of a tranexamic acid-peptide fusion in a peptide, to which tranexamic acid is linked, and have performed the experiments. As a result, they have discovered that some peptides in the tranexamic acid-peptide library inhibit melanin production and thus exhibit the skin whitening effect thereby completing the present invention.

Accordingly, an aspect of the present invention discloses tranexamic acid-peptides, exhibiting skin whitening effect, selected from the group consisting of Tranexamil-AS, Tranexamil-AT, Tranexamil-AP, Tranexamil-GP, Tranexamil-ES, Tranexamil-KK, Tranexamil-HK, Tranexamil-MY, Tranexamil-GH, Tranexamil-MA, Tranexamil-AH, Tranexamil-CC, Tranexamil-SA, Tranexamil-WA, Tranexamil-WE, Tranexamil-KD, Tranexamil-NA, Tranexamil-TS, Tranexamil-SS, Tranexamil-EC, Tranexamil-TA, Tranexamil-PF, Tranexamil-VS, Tranexamil-VV, Tranexamil-VP, Tranexamil-AA, Tranexamil-PS, Tranexamil-HA, Tranexamil-GK, Tranexamil-KV, Tranexamil-AR, Tranexamil-RP, Tranexamil-PQ, Tranexamil-QG, Tranexamil-PP, Tranexamil-VR, Tranexamil-SV, Tranexamil-ET, Tranexamil-CG, and Tranexamil-NT.

The present inventors have prepared various libraries of tranexamic acid-peptides containing tranexamic acid at their N-terminus, and have screened peptides with excellent inhibitory activity against melanin production among candidate peptides, and as a result, provide the tranexamic acid-peptides of the present invention.

As used herein, the term "peptide" refers to a linear molecule formed of amino acid residues linked together by peptide bonds, and a tranexamic acid-peptide refers to a form in which tranexamic acid is bound to the N-terminus of the peptide.

According to a preferred embodiment of the present invention, the peptide of the present invention can induce a modification by linking tranexamic acid to the N-terminus of the peptide. Through such modification, the peptide of the present invention can have a high half-life due to increased stability in vivo.

According to a preferred embodiment of the present invention, a modification may be induced by linking an amino group to the C-terminus of a peptide.

The above-mentioned modification of amino acids acts to significantly improve the stability of the peptide of the present invention. As used herein, the term "stability" not only refers to in vivo stability, but also storage stability (e.g., storage stability at room temperature). The above-mentioned protecting group acts to protect the peptides of the present invention from the attack of a protein cleaving enzyme in vivo.

Figure 6:
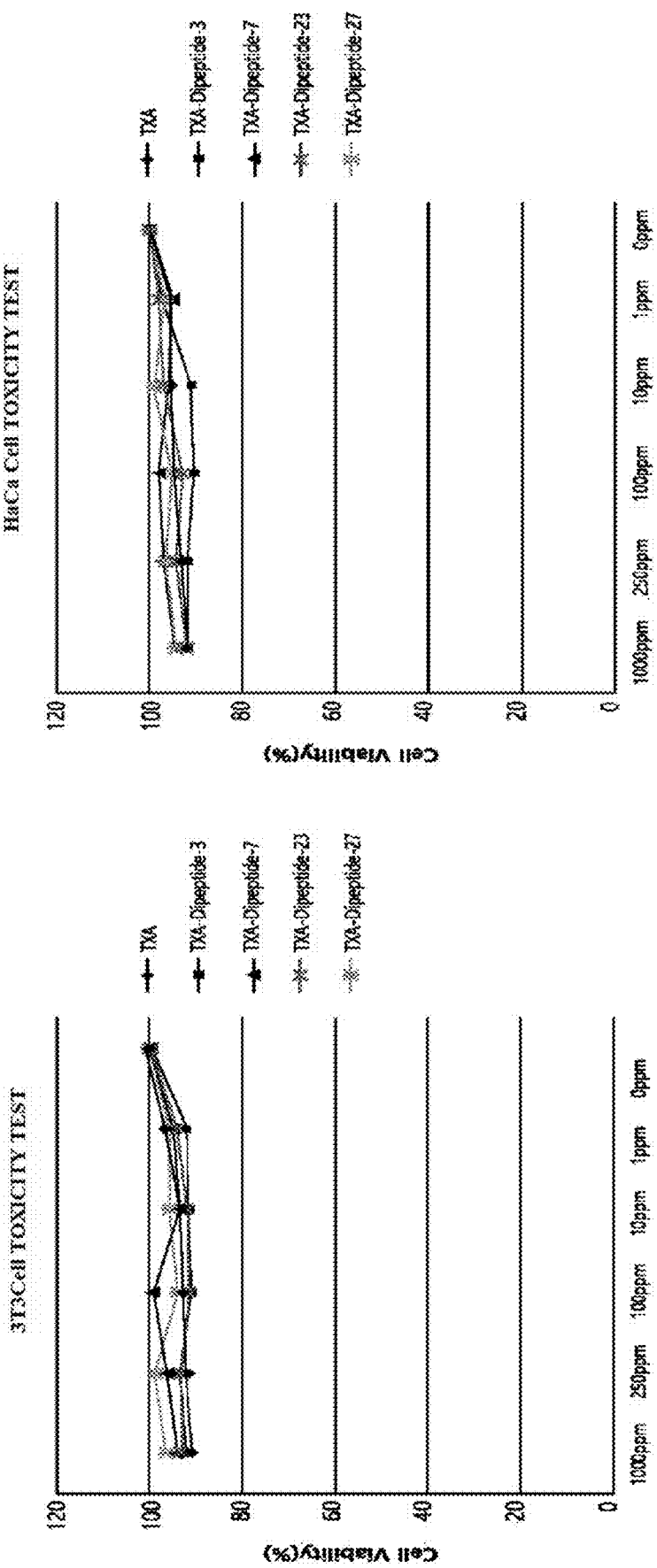
FIG. 6 shows graphs illustrating the cytotoxicity of tranexamic acid-peptides confirmed through the toxicity of NIH3T3 cells and HACAT cells.

According to a preferred embodiment of the present invention, the peptides of the present invention did not exhibit toxicity to human-derived cells, and thus is highly useful as a peptide for skin whitening. According to the present invention, when HaCat cells and NIH3T3 cells were treated with the tranexamic acid-peptide at a concentration of 100 ng/mL to 1,000 µg/mL, no significant cytotoxicity was measured, and even when shapes of these cells were confirmed by visual inspection, no significant change was observed (FIG. 6).

Figure 3:
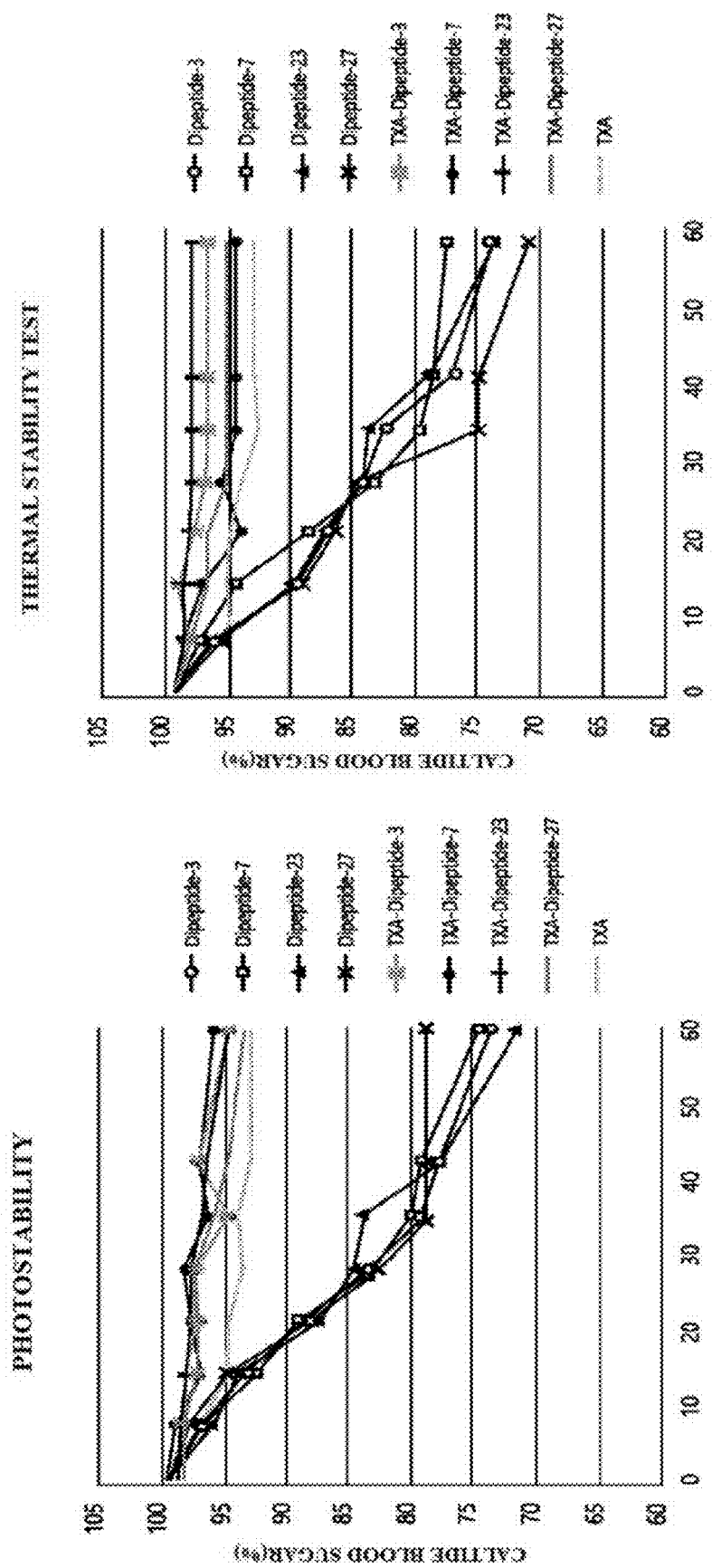
FIG. 3 is a graph illustrating the measurement results of tranexamic acid-peptides with regard to thermal stability and photostability.

According to the present invention, the tranexamic acid-peptides showed excellent thermal stability even at a temperature of 50° C. and it was confirmed to be stable even in the sunlight condition (FIG. 3). The peptides may be advantageously applied to products such as pharmaceutical drugs, quasi-drugs, and cosmetics, which require long-term storage.

According to a preferred embodiment of the present invention, the peptides of the present invention have the ability to inhibit melanin production. According to the present invention, when melanocytes were treated with -MSH to induce melanin production, treated with the tranexamic acid-peptides of the present invention, treated with the tranexamic acid-peptides of the present invention, cultured, and the amount of melanin production was compared, the melanin production was shown to be inhibited to a level of about 50% at maximum compared to that of the control group (Table 1).

Figure 1:
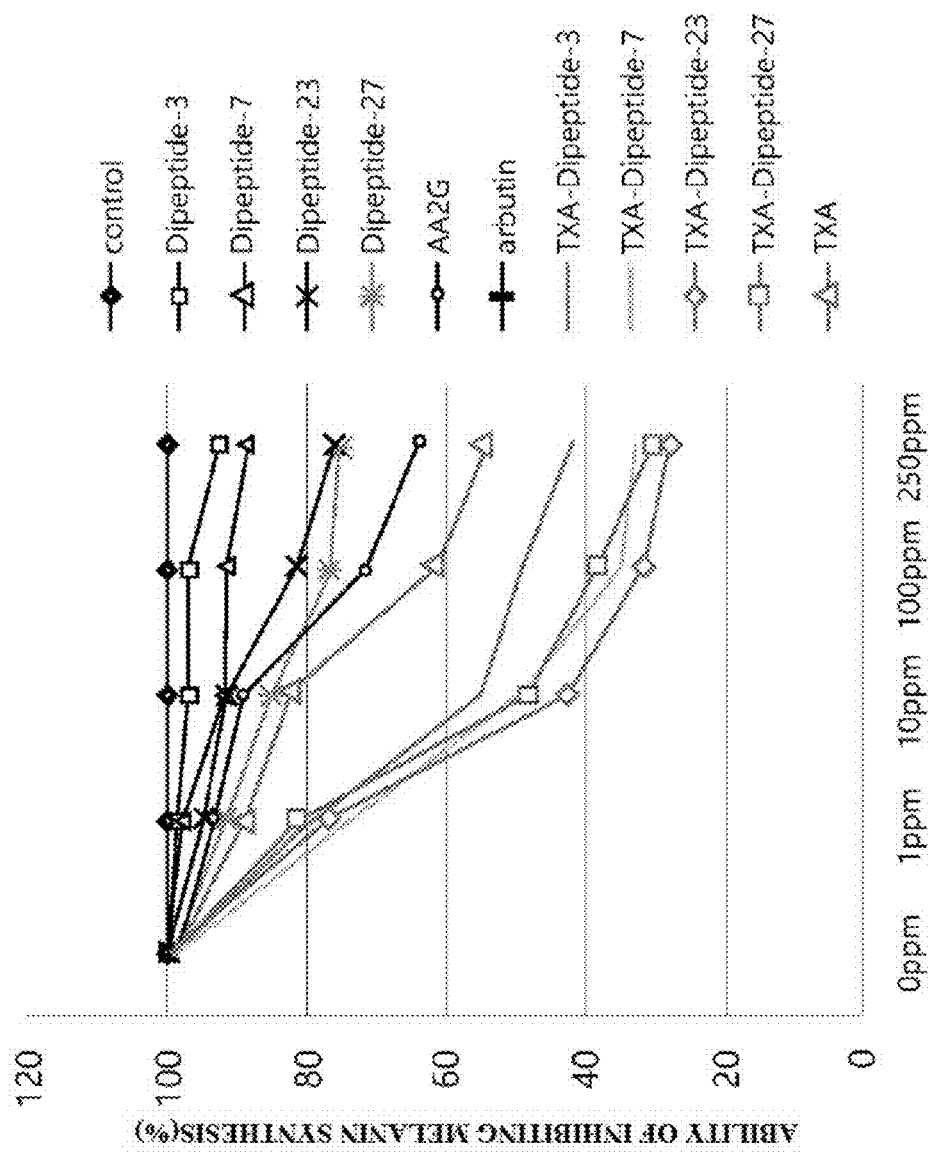
FIG. 1 is a graph illustrating the screening results of whitening with regard to a tranexamic acid-peptide library.
Figure 4:
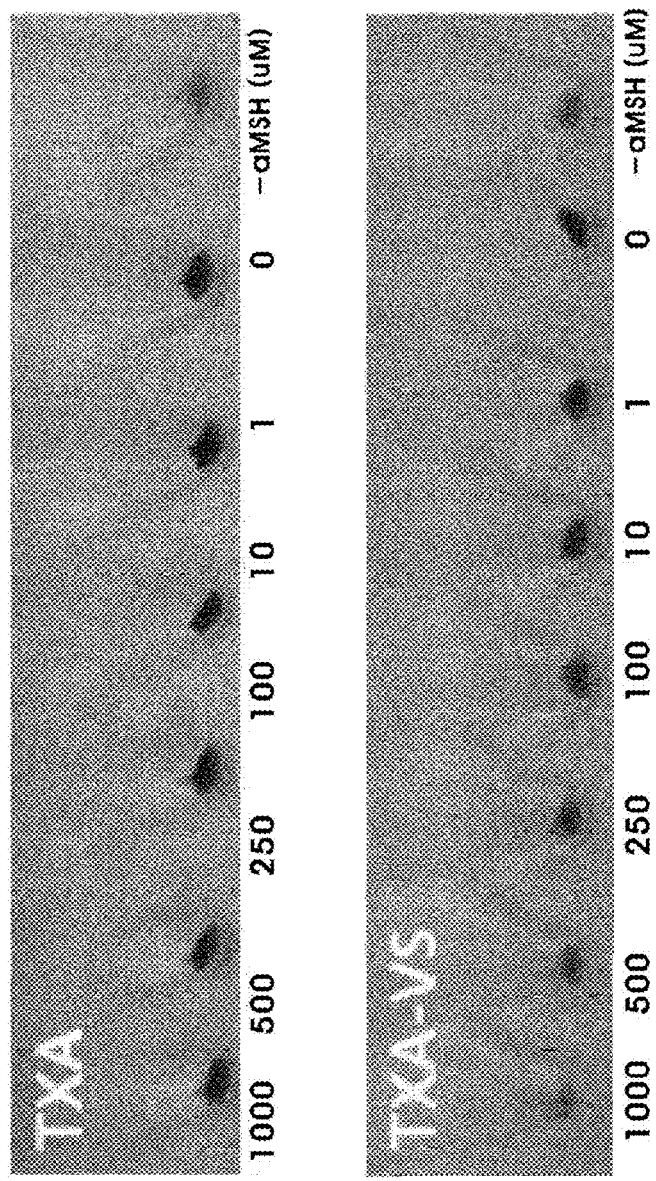
FIG. 4 shows graphs illustrating the comparison results with regard to the effect of reducing melanin production by melanocytes, after treating the B16F10 cells, which were treated with -MSH, with tranexamic acid-peptides.

According to a preferred embodiment of the present invention, the peptides of the present invention increase the melanin production in a concentration-dependent manner. According to the present invention, when cells were treated with the tranexamic acid-peptide (NA-PS) and the peptides, to which tranexamic acid was not bound, at various concentrations (1µ, 10µ, 100µ, and 250µ), cultured for 3 days, and the amount of melanin production in these cells was confirmed by visual inspection, it was confirmed that the amount of melanin production was decreased in a concentration-dependent manner (FIG. 4). Additionally, when cells were treated with 4 kinds of the tranexamic acid-peptides; the peptides, to which tranexamic acid was not bound; Arbutin; and AA2G at various concentrations (1µ, 10µ, 100µ, and 250µ), cultured for 3 days, and the absorbance of the cultures were measured at 490 nm and analyzed. As a result, it was confirmed that the amount of melanin production was significantly reduced in cells treated with the peptides, to which tranexamic acid was not bound, compared to cells treated with tranexamic acid-peptides (FIG. 1).

Figure 5:
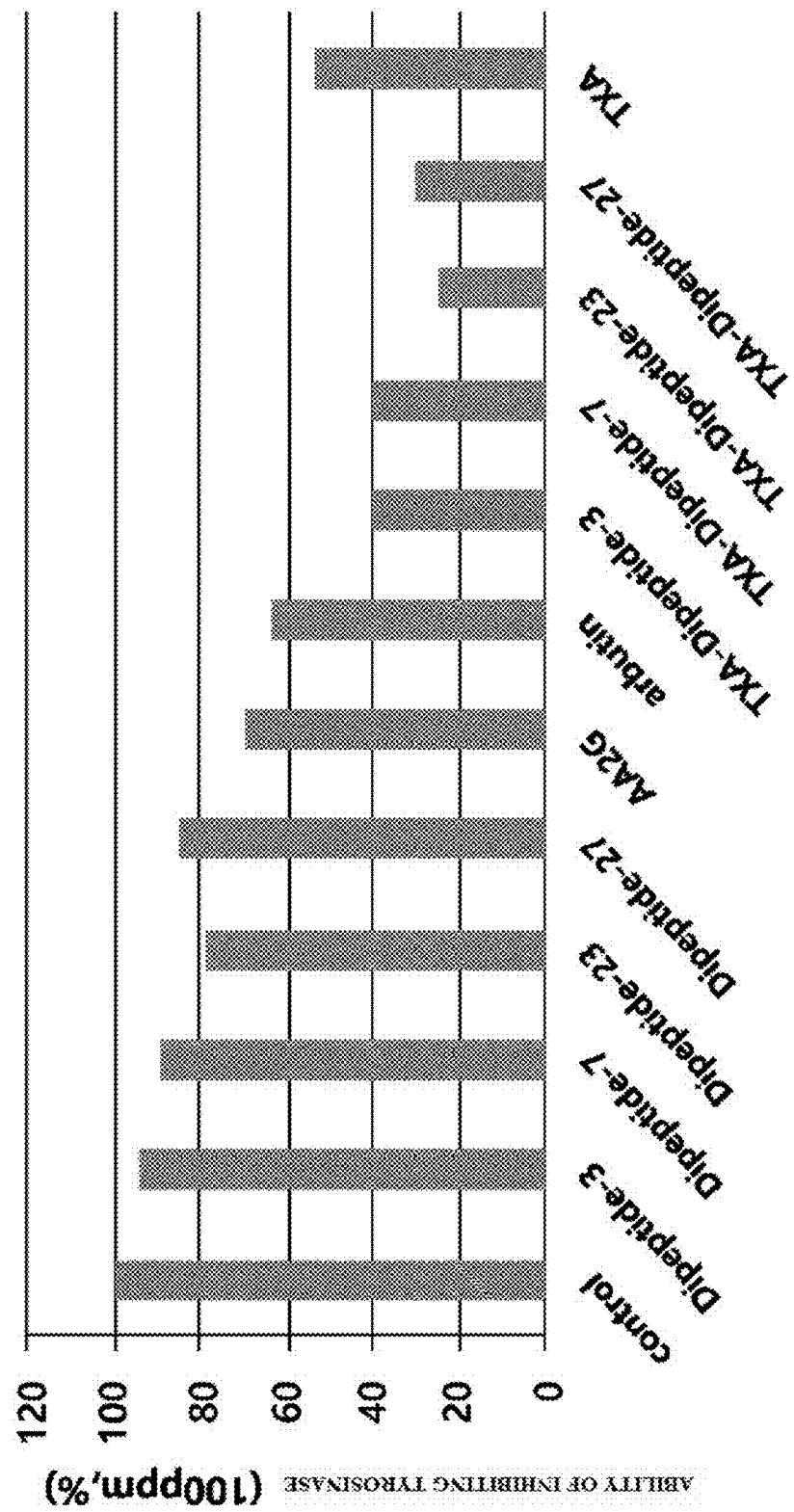
FIG. 5 is a graph illustrating the results of determining the inhibitory ability of tranexamic acid-peptides against tyrosinase according to concentration.

According to a preferred embodiment of the present invention, the peptides of the present invention inhibit the activity of tyrosinase. According to the present invention, when L-tyrosine, peptides, or tranexamic acid-peptides was reacted with tyrosinase, and the inhibitory rate against tyrosinase was confirmed by measuring the absorbance at 475 nm, it was confirmed that the treatment with the tranexamic acid-peptides showed a significant inhibitory effect against the activity of tyrosinase, compared to the treatment with peptides, to which tranexamic acid was not bound, and Arbutin (FIG. 5).

According to a preferred embodiment of the present invention, the peptides of the present invention inhibit the expression of microphthalmia-associated transcription factor (MITF). Melanin is produced by a series of enzymatic reactions (Olivares et al., *Pigment Cell Melanoma Res* 22(6): 750-760(2009)), and the major mechanism of melanin production is cell proliferation and increase of enzyme activity of tyrosinase. The most important enzyme in melanin production is tyrosinase, which is a rate-controlling factor that catalyzes the early stage in melanin biosynthesis, and tyrosine is converted into 3,4-dihydroxy-phenylalanine (DOPA) and DOPA quinone by tyrosinase, and thereby red-based melanin (pheomelanin) and brown-based eumelanin are synthesized (Lopezet et al., *J Biol Chem* 267: 381-390(1992)). Two other enzymes which are important in the formation of eumelanin are TRP-1 and TRP-2. Additionally, the microphthalmia-associated transcription factor (MITF) is an important element in charge of the transcription of tyrosinase and related enzymes (TRPs), and once the expression of MITF is inhibited and the production of melanin is supposed to be inhibited.

Figure 7:
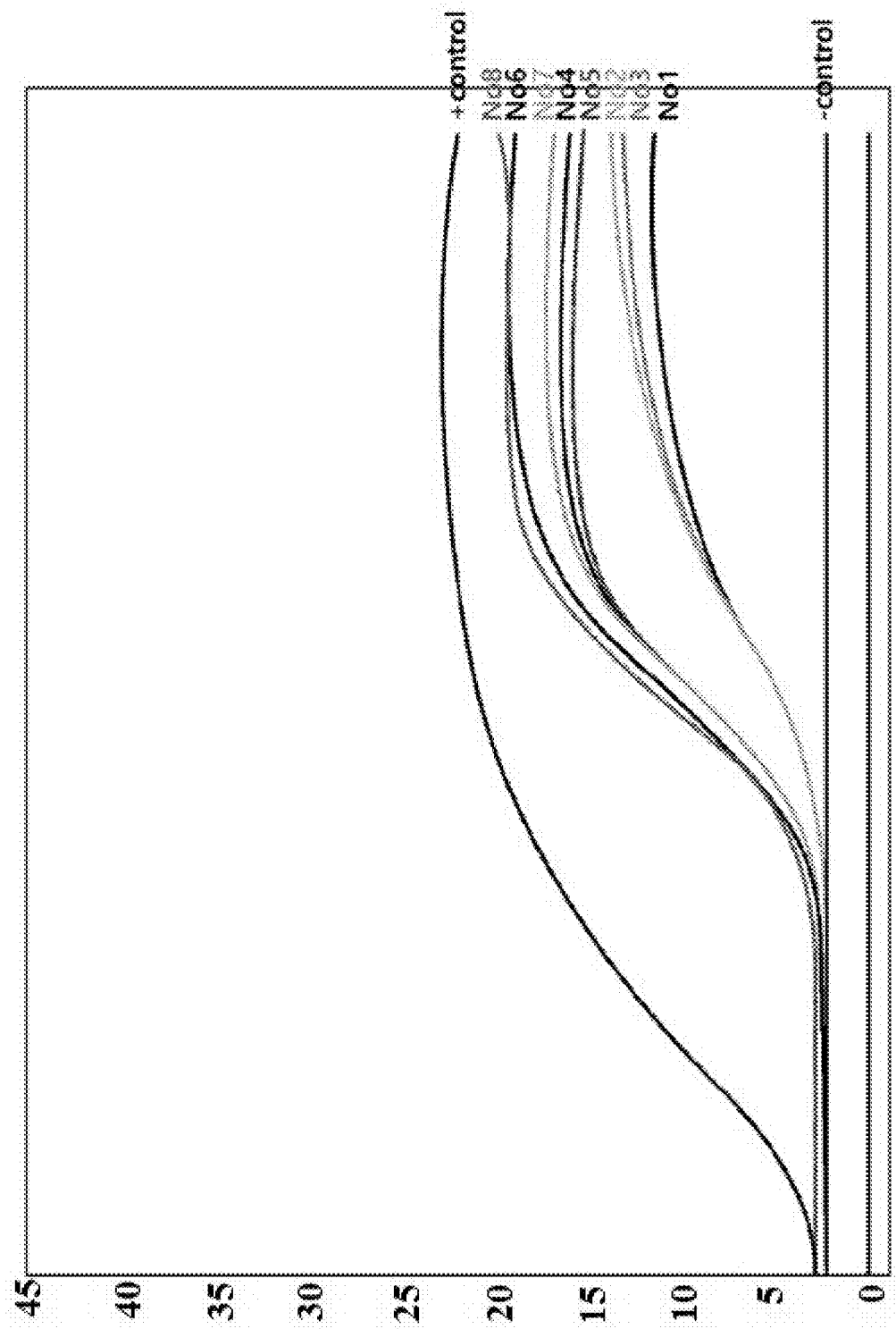
FIG. 7 is a graph illustrating the results of reverse transcription polymerase chain reaction (RT-PCR) performed using the microphthalmia-associated transcription factor (MITF) primers, in which the B16F10 cells, which were treated with -MSH, were treated with tranexamic acid-peptides, and then mRNAs were extracted.

According to the present invention, melanocytes were treated with -MSH and peptides (PS, VS); or -MSH and tranexamic acid-peptides (Tranexamyl-AP, Tranexamyl-HK, Tranexamyl-VS, Tranexamyl-PS) at various concentrations (1µ, 10µ, and 50µ), cultured for 4 days, and mRNAs were obtained from the cells and subjected to RT-PCR. As a result, it was confirmed that the treatment with the tranexamic acid-peptides inhibited the expression of the gene (MITF) associated with the melanin production (FIG. 7). These results indicate that the peptides of the present invention inhibit the expression of genes related to melanin production and thereby have a significantly excellent effect on skin whitening.

Additionally, in the case of a composition containing the peptides of the present invention, it may be used very effectively for skin whitening using various formulations.

Figure 9:
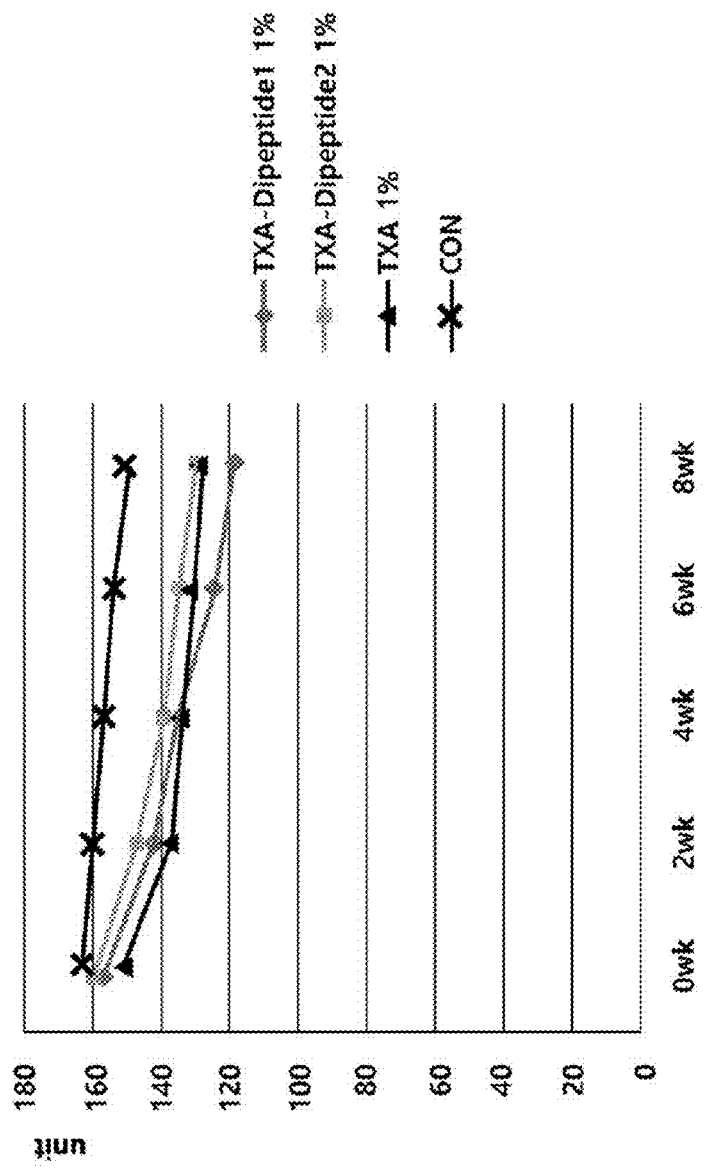
FIG. 9 is a graph illustrating the results of clinical whitening effects of creams containing 1% tranexamic acid-peptides.
Figure 10:
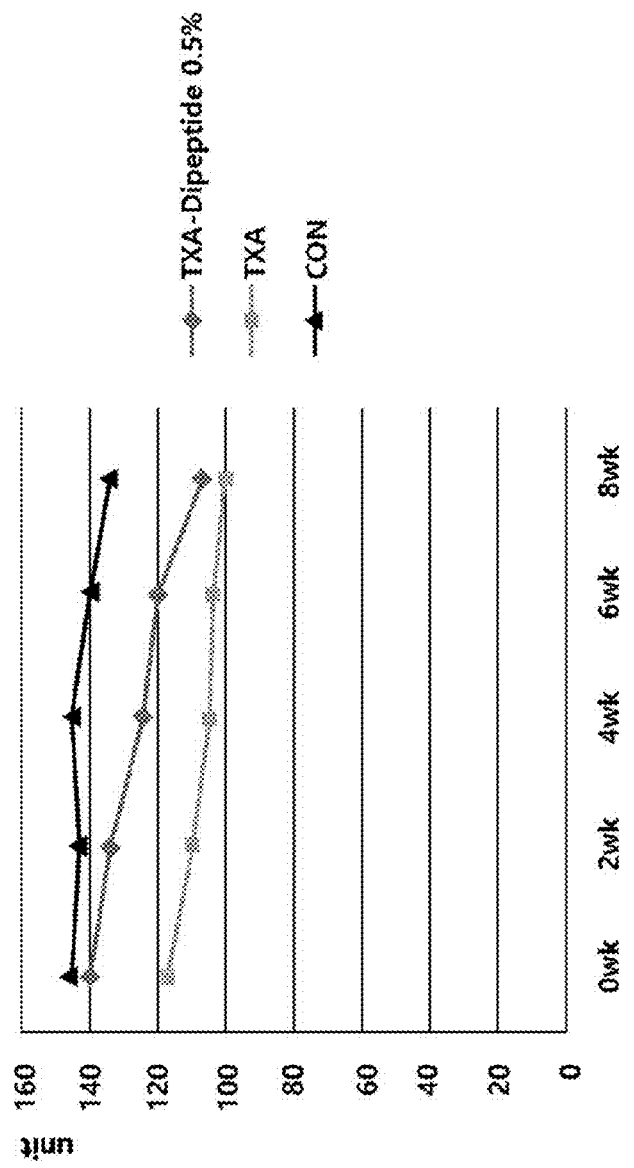
FIG. 10 is a graph illustrating the results of clinical whitening effects of creams containing 0.5% tranexamic acid-peptides.

To confirm the skin whitening effect of the tranexamic acid-peptides, creams containing the tranexamic acid-peptides were prepared and subjected to clinical tests. As a result, it was confirmed that tranexamic acid-peptides have an excellent whitening effect compared to pure tranexamic acid or the control group in clinical conditions (FIG. 9). Additionally, the same results were observed in experiments performed by lowering the content of tranexamic acid-peptides by half, and this indicates that a whitening effect can be maintained even when the content of tranexamic acid-peptides is lowered (FIG. 10).

Additionally, the second aspect of the present invention provides a skin whitening composition containing a tranexamic acid-peptide selected from the group consisting of Tranexamil-AS, Tranexamil-AT, Tranexamil-AP, Tranexamil-GP, Tranexamil-ES, Tranexamil-KK, Tranexamil-HK, Tranexamil-MY, Tranexamil-GH, Tranexamil-MA, Tranexamil-AH, Tranexamil-CC, Tranexamil-SA, Tranexamil-WA, Tranexamil-WE, Tranexamil-KD, Tranexamil-NA, Tranexamil-TS, Tranexamil-SS, Tranexamil-EC, Tranexamil-TA, Tranexamil-PF, Tranexamil-VS, Tranexamil-VV, Tranexamil-VP, Tranexamil-AA, Tranexamil-PS, Tranexamil-HA, Tranexamil-GK, Tranexamil-KV, Tranexamil-AR, Tranexamil-RP, Tranexamil-PQ, Tranexamil-QG, Tranexamil-PP, Tranexamil-VR, Tranexamil-SV, Tranexamil-ET, Tranexamil-CG, and Tranexamil-NT.

The composition of the present invention may be prepared as a cosmetic composition.

The tranexamic acid-peptides used as an active ingredient in the composition of the present invention are composed of 2 to 6 amino acid residues and has a very small molecular weight and thus has excellent skin permeability. Accordingly, when the composition of the present invention is topically applied to the skin, a skin whitening effect can be achieved due to a high skin penetration rate. The composition of the present invention inhibits the production of melanin, and thus it brightens skin color, keeps skin tone constant, and is effective in eliminating skin pigments and eliminating age spots. The tranexamic acid-peptides of the present invention inhibit the production of melanin pigments in keratinocytes by several processes, exhibit the effect of brightening the color of stratum corneum by preventing or weakening the release of melanin generated in keratinocytes.

The composition containing the tranexamic acid-peptides according to the present invention as an active ingredient may be applied to a pharmaceutical composition in a gel type, skin type, cream type, ointment type, etc., and a cosmetic composition, but the applicable types are not limited thereto. The above composition may be appropriately prepared by a known method, by adding a conventional softener, emulsifier, thickener, or other materials known in the art.

The gel-type composition may be prepared by adding a softener (e.g., trimethylolpropane, polyethylene glycol or glycerin, etc.), a solvent (e.g., propylene glycol, ethanol, isocetyl alcohol, etc.), purified water, etc.

The skin-type composition may be prepared by adding fatty alcohol (e.g., stearyl alcohol, myristyl alcohol, behenyl alcohol, arachidyl alcohol, isostearyl alcohol, isocetyl alcohol, etc.), butylene glycol, glycerin, allantoin, methylparaben, edetate-2-sodium, xanthan gum, dimethicone, polyethylene glycol-60 hydrogenoate castor oil, polysorbate 60, distilled water, etc.

The cream-type composition may be prepared by adding fatty alcohol (e.g., stearyl alcohol, myristyl alcohol, behenyl alcohol, arachidyl alcohol, isostearyl alcohol, isocetyl alcohol, etc.), lipids (e.g., lecithin, phosphatidylcholine, phosphatidylethanolamine, phosphatidylserine, phosphatidylinositol, etc.), derivatives thereof, emulsifiers (e.g., glyceryl stearate, sorbitan palmitate, sorbitan stearate, etc.), natural fat or oil (e.g., avocado oil, apricot oil, babassu oil, borage oil, camellia oil, etc.), a solvent (e.g., propylene glycol, etc.), distilled water, etc.

The ointment-type composition may be prepared by adding a softener, an emulsifier, and waxes (e.g., microcrystalline wax, paraffin, ceresin, beeswax, spermaceti, vaseline, etc.).

Additionally, the present invention may also be provided as a formulation containing one or more pharmaceutically acceptable carriers or excipients and the compositions as active ingredients.

Accordingly, the formulation may include a pharmaceutically acceptable carrier, diluent, excipient, or a combination thereof, as needed. These agents facilitate the administration of the active ingredient into an organism.

Hereinafter, the present invention will be described in further detail with reference to the following examples. However, the following examples are intended to illustrate the present invention and the scope of the present invention is not limited thereto.

EXAMPLES

Example 1: Synthesis of Library of Peptides

To synthesize a library of peptides, chlorotrityl of chloride resin, to which nsc-amino acid (nsc-Ala, nsc-Arg(pbf), nsc-Asp(OtBu), nsc-Asn(trt), nsc-Gly, nsc-Glu(OtBu), nsc-Gln (trt), nsc-His (trt), nsc-Ser (tBu), nsc-Thr (tBu), nsc-Tyr (tBu), nsc-Trp (Boc), nsc-Leu, nsc-Ile, nsc-Val, nsc-Phe, nsc-Met, nsc-Lys(Boc), nsc-Pro) are attached (CTL resin, Novabiochem Cat No. 01-64-0021), was added to each of 19 lines of a 96-well Teflon reactor per series, and 1 mL of methylene chloride (MC) was added thereto, and stirred for 3 minutes. After removing the solution, 1 mL of dimethylformamide (DM) was added thereto and stirred for minutes, and the solvent was removed again. The prepared tranexamic acid-peptidyl resin was washed 3 times with DMF, MC, and methanol, dried by slowing flowing nitrogen gas thereto, and then completely dried in vacuum under reduced pressure over P205. 30 mL of a mixed solution [including trifluroacetic acid: TFA) 81.5%, distilled water 5%, thioanisole 5%, phenol 5%, EDT (1,2-Ethanedithiol) 2.5%, and triisopropylsilane (TIS) 1%] was added to the prepared resin, and the reaction was maintained in an ice bath for 1 hour while intermittently shaking at room temperature. The resin was filtered, washed with a small amount of TFA solution, and combined with the mother liquid. Then, tranexamic acid-peptides were obtained.

As a result of synthesis and purification, 40 kinds of tranexamic acid-peptides to which peptides of mutually-different sequences were bound were obtained (Table 1). The yield of the synthesized tranexamic acid-peptides varied by the difference in physical properties due to the difference in peptide sequence, and the average yield was about 10%. During the column separation, although the elution time varied, the peak was found at the time zone of 8 minutes.

Example 2: Screening of Tranexamic Acid Peptides

B16F1 cells, which are mouse melanocytes, were cultured in Dulbecco's modified Eagle's media (DMEM, Sigma), to which 10% fetal bovine serum (FBS, Sigma) was added, under 37° C. $CO_2$ conditions. The cells were cultured in a 24-well plate at a concentration of $1\times10^5$ cells/well, and the attachment of cells was confirmed. Then, the control group was not treated with anything but only a solvent was added thereto, whereas a-MSH (20 µg/mL) was added to the positive control group. The remaining dishes were treated with α-MSH (20 μg/mL), 40 kinds of tranexamic acid-peptides, and the control group with Arbutin and AA2G, to a concentration of 1 μg/mL, 10 μg/mL, 100 μg/mL, and 250 μg/mL, respectively. Test materials were added to each dish and cultured for 3 days. After 3 days, the culture was removed by centrifugation, and the cells were lysed and intracellular melanin was collected, and observed at 490 nm to measure the amount of intracellular melanin production.

Figure 2:
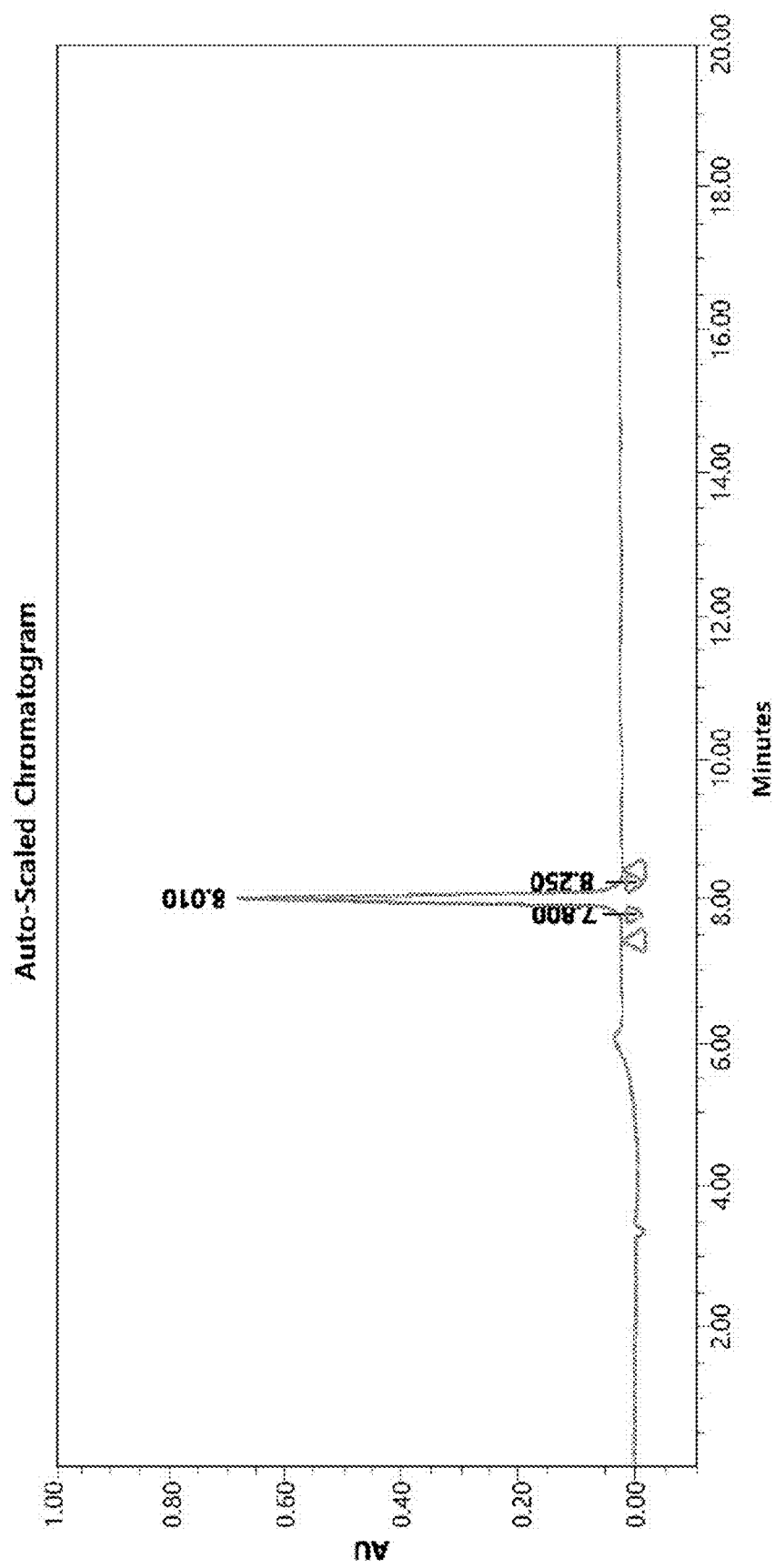
FIG. 2 is a graph illustrating the results of high performance liquid chromatography (HPLC) analysis with regard to tranexamic acid-peptides.

40 kinds of tranexamic acid-peptides were treated according to concentration, and their inhibitory effect against melanin production was measured. It was confirmed that the amount of melanin was rapidly reduced in the group treated with peptides to which tranexamic acid was bound, compared to the comparative group in which tranexamic acid was not bound to peptides. Additionally, in the case of 4 kinds of synthesized tranexamic acid-peptides (Tranexamil-AP, -HK, -VS, and -PS) with excellent inhibitory effect against α-MSH (%), these tranexamic acid-peptides were shown to be superior to Arbutin and AA2G, which are the existing materials with a whitening function (FIG. 2). From these results, it is thought that when factors that induce melanin production in the skin are applied, the synthesized tranexamic acid-dipeptides can inhibit their activity thereby brightening the skin tone.

The candidate peptides which showed good titers by screening were classified into a separate group and prepared on a large scale and subjected to experiments. Table 1 shows the results of screening the tranexamic acid-peptides.

TABLE 1

| No. | Species | α-MSH Inhibitory Ability (%) |
|---|---|---|
| 1 | Control (No Treatment) | 100 |
| 2 | Dipeptide-1 AS | 98 |
| 3 | Dipeptide-2 AT | 88 |
| 4 | Dipeptide-3 AP | 41 |
| 5 | Dipeptide-4 GP | 80 |
| 6 | Dipeptide-5 ES | 80 |
| 7 | Dipeptide-6 KK | 83 |
| 8 | Dipeptide-7 HK | 32 |
| 9 | Dipeptide-8 MY | 78 |
| 10 | Dipeptide-9 GH | 70 |
| 11 | Dipeptide-10 MA | 56 |
| 12 | Dipeptide-11 AH | 82 |
| 13 | Dipeptide-12 CC | 83 |
| 14 | Dipeptide-13 SA | 81 |
| 15 | Dipeptide-14 WA | 65 |
| 16 | Dipeptide-15 WE | 78 |
| 17 | Dipeptide-16 KD | 81 |
| 18 | Dipeptide-17 NA | 79 |
| 19 | Dipeptide-18 TS | 75 |
| 20 | Dipeptide-19 SS | 80 |
| 21 | Dipeptide-20 EC | 61 |
| 22 | Dipeptide-21 TA | 76 |
| 23 | Dipeptide-22 PF | 89 |
| 24 | Dipeptide-23 VS | 24 |
| 25 | Dipeptide-24 VV | 72 |
| 26 | Dipeptide-25 VP | 69 |
| 27 | Dipeptide-26 AA | 92 |
| 28 | Dipeptide-27 PS | 28 |
| 29 | Dipeptide-28 HA | 87 |
| 30 | Dipeptide-29 GK | 96 |
| 31 | Dipeptide-30 KV | 83 |
| 32 | Dipeptide-31 AR | 93 |
| 33 | Dipeptide-32 RP | 87 |
| 34 | Dipeptide-33 PQ | 71 |
| 35 | Dipeptide-34 QG | 85 |
| 36 | Dipeptide-35 PP | 85 |
| 37 | Dipeptide-36 VR | 70 |
| 38 | Dipeptide-37 SV | 64 |
| 39 | Dipeptide-38 ET | 52 |
| 40 | Dipeptide-39 CG | 92 |
| 41 | Dipeptide-40 NT | 84 |
| 42 | TXA | 45 |

Example 3: Experiment for Confirming Stability of Tranexamic Acid-Peptides

To confirm the thermal stability and photostability of the prepared peptides, Tranexamyl-AP, Tranexamyl-HK, Tranexamyl-VS, and Tranexamyl-PS, which have high purity of at least 98% purified using HPLC, were dissolved in 50 mM Tris-HCl (pH 8.0) buffer to have a concentration of 100 μg/mL, aliquoted into glass vials, and stored at 50° C. for 7, 14, 21, 28, 35, 42, and 60 days, and the loss of peptides by heat was measured, and the stability was measured under the sunlight condition using the same method (FIG. 3). As a result of measurement of loss of peptides by heat and measurement of stability under the sunlight condition, only less than 10% of loss of peptides was shown thus confirming that these tranexamic acid-peptides have high stability against heat and during the storage period. Additionally, the results of comparative stability experiment showed that the tranexamic acid-dipeptides had a higher amount by about 20% on average, compared to the peptides to which tranexamic acid was not bound. Conclusively, it was confirmed that tranexamic acid-peptides were more stable under the heat and sunlight, compared to the peptides to which tranexamic acid was not bound.

Example 4: Confirmation of Whitening Effect of Tranexamic Acid-Peptides

Tranexamic acid-peptides were treated according to concentration and their inhibitory effect against melanin production was measured. The mouse melanocytes were cultured in Dulbecco's modified Eagle's media (DMEM, Sigma) containing 10% fetal bovine serum (BSA, Sigma) under 37° C. $CO_2$ conditions.

The cells were cultured in a 24-well plate at a concentration of $1 \times 10^5$ cells/well, and the attachment of cells was confirmed. Then, the control group was not treated with anything but only a solvent was added thereto, whereas a-MSH (20 j) was added to the positive control group. The remaining dishes were treated with α-MSH (20 μg/mL), 4 kinds of tranexamic acid-peptides, and the control group with Arbutin and AA2G, to a concentration of 1 μg/mL, 10 μg/mL, 100 μg/mL, and 250μ), respectively. Test materials were added to each dish and cultured for 3 days. After 3 days, the culture was removed by centrifugation, and the amount of intracellular melanin production was confirmed by visual inspection.

FIG. 4 shows the images of the produced melanocytes confirming the decrease rate of melanin production according to each concentration of tranexamic acid-peptides and VS peptide. From the images, it was observed that the cell number did not decrease relatively compared to that treated with α-MSH, whereas the cell number was rapidly decreased where Arbutin, etc. was treated at similar concentrations. From the result that the amount of melanin production was decreased compared to the number of cells, it was found that the tranexamic acid-peptides have an inhibitory effect against melanin production.

Example 5: Decrease of Tyrosinase Activity by Tranexamic Acid-Peptides

Tyrosinase, an enzyme known to be involved in the biosynthesis of melanin, acts as a catalyst in the process of melanin biosynthesis starting from L-tyrosine, and in the oxidation processes of from tyrosine to 3,4-dihydroxy-L-phenylananine (DOPA) and from DOPA to dopaquinone. Since the subsequent reactions after these two oxidation reactions occur spontaneously, the reactions in which tyrosinase is involved determine the entire reaction rate. For this reason, tyrosinase inhibitory activity is a very important factor in evaluating whitening activity. In this experiment, in vitro tyrosinase inhibitory activity of synthesized tranexamic acid dipeptides was compared (FIG. 5).

L-tyrosin, as a substrate, was dissolved in a phosphate buffer (0.05 M, pH 6.8) to a concentration of 1.5 mM, and the resulting solution (0.01 mL) was added to a 0.3 mL spectrophotometer cuvette and 0.01 mL of L-DOPA (cofactor), which was prepared at a concentration of 0.06 mM, was added thereto. The peptides of the present invention were added thereto and the phosphate buffer solution was added to 0.1 mL. The reaction was performed by adding thereto 0.1 mL of an enzyme solution, in which tyrosinase was dissolved in a phosphate buffer at 60 U/mL. Additionally, each of Arbutin, tranexamic acid-peptides, and peptides, to which tranexamic acid is not bound, was added in an amount of 100 ppm to perform a comparative experiment. In particular, as the control group (blank), only 0.1 mL of a buffer was added instead of tyrosinase. The reaction was performed at 37° C. for 10 minutes, and the absorbance was measured at 475 nm using a spectrophotometer (Beckman DU-7500) to obtain the inhibition rate against tyrosinase (FIG. 5). As a result of the experiment, it was confirmed that the 4 kinds of tranexamic acid-peptides showed a relatively higher tyrosinase inhibitory effect compared to AA2G or Arbutin, and that the peptides, to which tranexamic acid is not bound, did not have a good inhibitory effect.

Example 6: Experiment on Cytotoxicity

To confirm whether the peptides of the present invention had cytotoxicity in the keratinocytes, the cytotoxicity was evaluated using the MTT assay. HACAT cells and 3T3 cells were seeded to each well of a 24-well plate at a concentration of $4 \times 10^4$ cells/24 well, and cultured at a constant temperature under 37° C. $CO_2$ conditions. The culture was washed twice with PBS, cultured, and treated with the synthesized tranexamic acid dipeptides at various concentrations (1 mg/mL to 1 µg/mL), and cultured at the constant temperature for 24 hours. After the cultivation, the MTT 0.5% in DPBS was mixed with culture medium at 1:9 (v/v) ratio and added thereto, and cultured in a $CO_2$ incubator for 2 hours. The produced formazan was dissolved in DMSO and its absorbance was measured at 570 nm by ELISA. As can be seen in FIG. 6, with respect to HACAT cells (a kind of keratinocyte) and 3T3 cells (a kind of fibroblast), the decrease of cell number by the peptides, which were administered at a low concentration to a high concentration, was not observed, and no significant change was observed even in microscopic observation of these cells.

From the above results, it was confirmed that tranexamic acid-peptides have no cytotoxicity on skin-related cells, and thus, it can be expected that these peptides of the present invention can be safely administered to the skin without causing any serious effect.

Example 7: Inhibition of Melanin-Producing Markers

To more clearly verify the whitening activity of tranexamic acid-peptides in mouse melanoma cells induced melanin production by -MSH treatment, the RNA production of microphthalmia-associated transcription factor (MITF) was confirmed by real-time reverse transcription polymerase chain reaction (qRT-PCR).

First, the B16F10 cells cultured in Example 2 were treated with two kinds of tranexamic acid-peptides (TXA-VS and TXA-PS) at a concentration of 0.1% and 0.05%, respectively. Then, for the real-time PCR measurement, RNA samples were extracted as follows.

The extraction was performed using intron RNA extraction kit (Intron Inc., Korea). Specific experimental methods are as follows.

(1) $1 \times 10^6$ cells in a 1.5 mL tube
(2) Remove medium by centrifugation at 13,000 rpm for 10 seconds, and
(3) Add 1 mL of a lysis buffer.
(4) Vigorously vortex.
(5) Add 200 µL of chloroform and vortex.
(6) Centrifuge at 13,000 rpm at 4° C. for 10 minutes. Transfer 400 µL to an empty tube.
(7) Add 400 µL of a binding buffer along with a Mix, and smoothly pipettes 2 or 3 times
(8) Place onto a column.
(9) Centrifuge at 13,000 rpm for 30 seconds.
(10) Wash with 700 µL of buffer A
(11) Close the cap of the tube and centrifuge at 13,000 rpm for 30 seconds.
(12) Repeat 10 to 11 times with buffer B.
(13) Dry at 13,000 rpm for 1 to 2 minutes.
(14) Add 50 µL of an elution buffer to the column and incubate at room temperature for 1 minute.
(15) Centrifuge at 13,000 rpm for 1 minute.

Real-time PCR was performed to confirm the expression amount of MITF using the extracted RNA, and the reagents and conditions used in the experiment are as follows.

Real-time PCR reagent: RealMOD™green qRT-PCR Mix (INTRON Inc.)

Primer: MITF, GAPDH (prepared by Bioneer Corporation)

PCR primer sequence, PCR mix composition, and PCR reaction conditions are shown in Tables 2, 3, and 4, respectively.

TABLE 2

| Primer name | SEQUENCE (5'-→3') |
|---|---|
| fMITF | GGCCAAGGCAGAGCAACTT (SEQ ID NO: 1) |
| rMITF | GCCCATGGTGGCAAGCT (SEQ ID NO: 2) |
| fGAPDH | ATCCCATCACCATCTTCCAG (SEQ ID NO: 3) |
| rHAPDH | CCATCACGCCACAGTTTCC (SEQ ID NO: 4) |

TABLE 3

|  | 1x |  |
|---|---|---|
| qRT-PCR | 10 | 10 |
| $E_{n2}$ Mix | 0.4 | 0.4 |
| primer 1 |  | 1 |
| primer 2 |  | 1 |
| RNA | 1 | 1 |
| Water | 8.6 | 6.6 |
|  | Total 20 µL |  |

TABLE 4

|  | temp. (° C.) | times | cycles |
|---|---|---|---|
| cDNA synthesis | 42 | 15 mins | 1 |
| Enzyme activation | 95 | 10 mins | 1 |
| Denaturation | 95 | 15 sec | 45 |
| annealing/extension | 45 | 60 sec | 45 |

Figure 8:
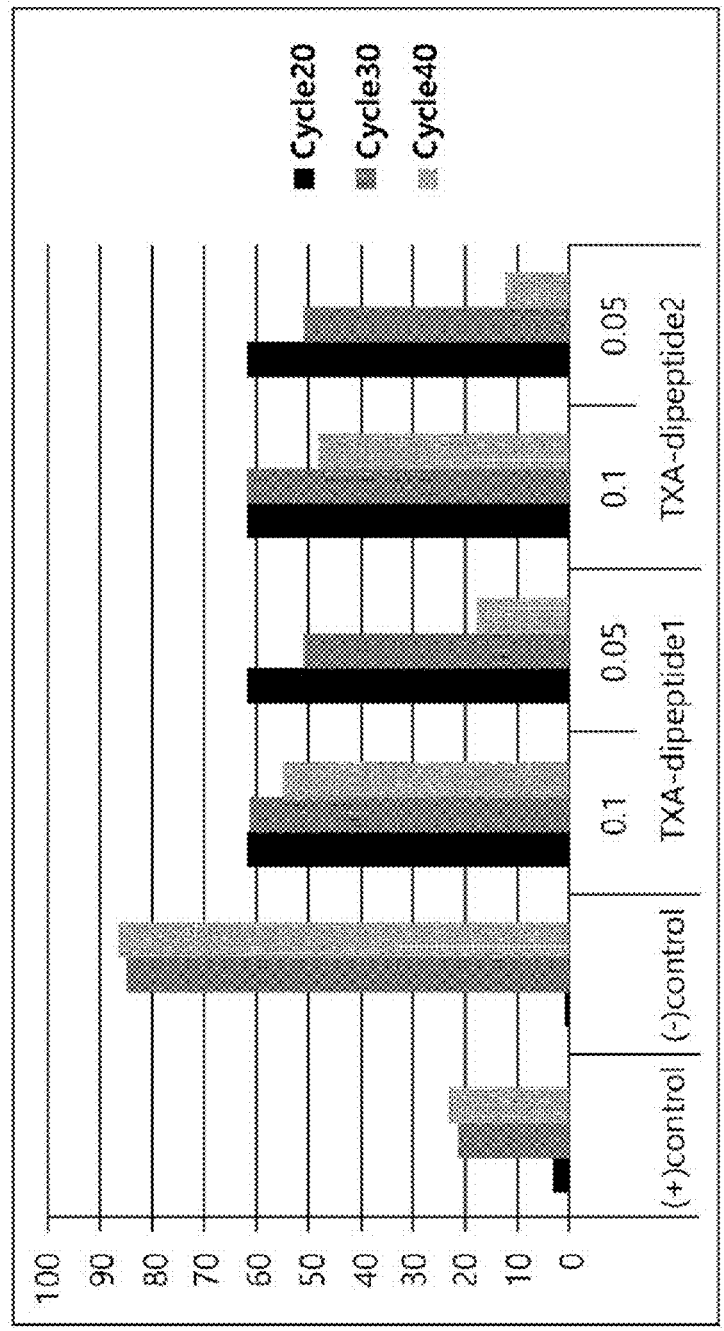
FIG. 8 is a graph illustrating the comparison results with regard to clinical whitening effect between tranexamic acid-peptides and tranexamic acid confirmed through clinical tests.

As a result of the experiment, as shown in FIGS. 7 and 8, it was confirmed that tranexamic acid-peptides of the present invention inhibit the expression of MITF, a gene related to melanin production, in a concentration-dependent manner.

Example 8: Gel-Type Compositions Containing Tranexamic Acid-Peptides

Gel-type compositions, which contain one or a plurality of tranexamic acid-peptides prepared in Example 2 and consist of the compositions in Table 2 below, were prepared according to the synthesis method of common gel-type compositions.

TABLE 5

| Ingredient | Weight (%) |
|---|---|
| Tranexamic acid-peptide | 1 |
| Carboxyvinyl polymer | 1.0 |
| Triethanolamine | 1.0 |
| Butylene glycol | 5.0 |
| Glycerin | 10.0 |
| Hydrogenated | 1.0 |
| Preservative, Fragrance | adequate amount |
| Distilled water | remaining amount |
| Total | 100 |

Example 9: Skin-Type Compositions Containing Tranexamic Acid-Peptides

Skin-type compositions, which contain one or a plurality of tranexamic acid-peptides prepared in Example 2 and consist of the compositions in Table 3 below, were prepared according to the synthesis method of common skin-type compositions.

TABLE 6

| Ingredient | Weight (%) |
|---|---|
| Tranexamic acid-peptide | 1 |
| Concentrated glycerin | 10 |
| Propylene glycol | 10 |
| Polyoxyethylene hydrogenated castor oil (E040) | 1.0 |
| Aqueous solution of sodium hyaluronate (1%) | 5.0 |
| Ethanol | 5.0 |
| Preservative, Fragrance | adequate amount |
| Distilled water | remaining amount |
| Total | 100 |

Example 10 Cream-Type Composition Containing Tranexamic Acid-Peptides

Gel-type compositions, which contain one or a plurality of tranexamic acid-peptides prepared in Example 2 and consist of the compositions in Table 4 below, were prepared according to the synthesis method of common gel-type compositions.

TABLE 7

| Ingredient | Weight (%) |
|---|---|
| Tranexamic acid-peptide | 1 |
| Stearyl alcohol | 6.0 |
| Stearic acid | 2.0 |
| Concentrated glycerin | 1.0 |
| Squalane | 9.0 |
| 1,3-butylene glycol | 6.0 |
| Polysorbate 60 | 1.5 |
| Polyethylene glycol 1000 | 4.0 |
| Hydrogenated Lanolin | 4.0 |
| Octyldodecanol | 10.0 |
| Sorbitan stearate | 0.8 |
| Triethanolamine | 0.5 |
| Preservative, Fragrance | adequate amount |
| Distilled water | remaining amount |
| Total | 100 |

Experimental Example: Clinical Test

Among the 4 kinds of tranexamic acid-dipeptides which showed high inhibitory effects against melanin synthesis in Example 2, two kinds (VS and PS) were selected, and thereby two kinds of creams containing 1% of tranexamic acid-dipeptides were prepared to have the same composition as in Example 10 below, and to confirm the skin whitening effect of these peptides, 54 women who had skin pigmentation but without an organic disease were collected. In particular, a cream containing tranexamic acid was used as the positive control group and the standard base cream was used as the negative control group.

The face of each subject was divided into two parts vertically and the two kinds of creams prepared above were applied to each face. The subjects were required to continuously use the creams in the morning and evening, 2 times a day for 8 weeks after washing the face.

For the objective evaluation of changes in skin pigmentation before and after the use of the creams, the changes in pigmentation were measured using the Mexameter (CK, Germany) before the use of the creams, 2 weeks, 4 weeks, 6 weeks, and 8 weeks after the use of the creams. The measurement results are shown in FIG. 9.

As shown in FIG. 9, it was confirmed that the creams containing the two kinds of tranexamic acid-dipeptides both had a greater whitening effect compared to the negative control group and the positive control group which contained only tranexamic acid. Additionally, after reviewing the weekly change rate of the melanin index, it was confirmed that, after 8 weeks, group 1 with tranexamic acid-dipeptide (VS) showed a decrease of 22.9%, group 2 with tranexamic acid-dipeptide (PS) showed a decrease of 183.2%, the tranexamic acid group showed a decrease of 11.4%, and the group with a base cream showed a decrease of 6.6% (FIG. 9).

As a result of the above experiment, the tranexamic acid-dipeptide with a greater effect between the two kinds of tranexamic acid-dipeptides, was selected and, as an attempt to reduce the content in the cream, a cream containing 0.5% tranexamic acid-dipeptide was prepared. Ten women subjects were collected and the 8-week clinical experiment was performed in the same manner as described above.

As shown in FIG. 10, it was confirmed that the cream containing 0.5% tranexamic acid-dipeptide had a greater whitening effect compared to the cream containing only tranexamic acid and the base cream. Additionally, after reviewing the weekly change rate of the melanin index, it was confirmed that, after 8 weeks, group 1 with 0.5% tranexamic acid-dipeptide (VS) showed a decrease of 23.9%, the group with tranexamic acid showed a decrease of 10.2%, and the group with the base cream showed a decrease of 4.7%.

Although the particular features of the present invention are described in detail above, it is apparent to those of ordinary skill in the art that these specific descriptions are only preferred embodiments and the scope of the present invention is not limited by these embodiments. Accordingly, the actual scope of the present invention will be defined by the appended claims and equivalents thereof.

Tranexamil-SS, Tranexamil-EC, Tranexamil-TA, Tranexamil-PF, Tranexamil-VS, Tranexamil-VV, Tranexamil-VP, Tranexamil-AA, Tranexamil-PS, Tranexamil-HA, Tranexamil-GK, Tranexamil-KV, Tranexamil-AR, Tranexamil-RP, Tranexamil-PQ, Tranexamil-QG, Tranexamil-PP, Tranexamil-VR, Tranexamil-SV, Tranexamil-ET, Tranexamil-CG and Tranexamil-NT.

2. The method of claim 1, wherein the tranexamic acid-peptide inhibits melanin synthesis.

3. The method of claim 1, wherein the tranexamic acid-peptide inhibits the activity of tyrosinase.

The invention claimed is:

1. A skin whitening method, comprising:
    administering to a subject a cosmetic composition comprising a tranexamic acid-peptide having skin whitening activity selected from the group consisting of Tranexamil-AS, Tranexamil-AT, Tranexamil-AP, Tranexamil-GP, Tranexamil-ES, Tranexamil-KK, Tranexamil-HK, Tranexamil-MY, Tranexamil-GH, Tranexamil-MA, Tranexamil-AH, Tranexamil-CC, Tranexamil-SA, Tranexamil-WA, Tranexamil-WE, Tranexamil-KD, Tranexamil-NA, Tranexamil-TS, Tranexamil-SS, Tranexamil-EC, Tranexamil-TA, Tranexamil-PF, Tranexamil-VS, Tranexamil-VV, Tranexamil-VP, Tranexamil-AA, Tranexamil-PS, Tranexamil-HA, Tranexamil-GK, Tranexamil-KV, Tranexamil-AR, Tranexamil-RP, Tranexamil-PQ, Tranexamil-QG, Tranexamil-PP, Tranexamil-VR, Tranexamil-SV, Tranexamil-ET, Tranexamil-CG and Tranexamil-NT.

2. The method of claim 1, wherein the tranexamic acid-peptide inhibits melanin synthesis.

3. The method of claim 1, wherein the tranexamic acid-peptide inhibits the activity of tyrosinase.

4. The method of claim 1, wherein the tranexamic acid-peptide inhibits the expression of microphthalmia-associated transcription factor (MITF).

5. The method of claim 1, wherein the tranexamic acid-peptide has a skin whitening effect at a concentration of 0.01% to 5.0%.

6. The method of claim 1, wherein the tranexamic acid-peptide has increased stability by the tranexamic acid at its N-terminus.

* * * * *

SEQUENCE LISTING

```
<160> NUMBER OF SEQ ID NOS: 4

<210> SEQ ID NO 1
<211> LENGTH: 19
<212> TYPE: DNA
<213> ORGANISM: Artificial Sequence
<220> FEATURE:
<223> OTHER INFORMATION: Primer: fMITF

<400> SEQUENCE: 1
ggccaaggca gagcaactt                                                19

<210> SEQ ID NO 2
<211> LENGTH: 17
<212> TYPE: DNA
<213> ORGANISM: Artificial Sequence
<220> FEATURE:
<223> OTHER INFORMATION: Primer: rMITF

<400> SEQUENCE: 2
gcccatggtg gcaagct                                                  17

<210> SEQ ID NO 3
<211> LENGTH: 20
<212> TYPE: DNA
<213> ORGANISM: Artificial Sequence
<220> FEATURE:
<223> OTHER INFORMATION: Primer: fGAPDH

<400> SEQUENCE: 3
atcccatcac catcttccag                                               20

<210> SEQ ID NO 4
<211> LENGTH: 19
<212> TYPE: DNA
<213> ORGANISM: Artificial Sequence
<220> FEATURE:
<223> OTHER INFORMATION: Primer: rHAPDH

<400> SEQUENCE: 4
ccatcacgcc acagtttcc                                                19
```